(12) United States Patent
Jeong et al.

(10) Patent No.: US 12,262,975 B2
(45) Date of Patent: Apr. 1, 2025

(54) INTRAORAL SCANNER HAVING TOMOGRAPHIC IMAGING FUNCTION AND METHOD FOR TOMOGRAPHIC IMAGING OF ORAL CAVITY USING THE SAME

(71) Applicants: HUVITZ CO., LTD., Anyang-si (KR); OSSVIS CO., LTD., Anyang-si (KR)

(72) Inventors: Hyo Sang Jeong, Anyang-si (KR); Min Soo Cho, Anyang-si (KR); Su Min Han, Anyang-si (KR); Weon Joon Lee, Anyang-si (KR)

(73) Assignees: HUVITZ CO., LTD., Anyang-si (KR); OSSVIS CO., LTD., Anyang-si (KR)

( * ) Notice: Subject to any disclaimer, the term of this patent is extended or adjusted under 35 U.S.C. 154(b) by 221 days.

(21) Appl. No.: 18/070,672

(22) Filed: Nov. 29, 2022

(65) Prior Publication Data
US 2023/0172454 A1 Jun. 8, 2023

(30) Foreign Application Priority Data
Dec. 3, 2021 (KR) .................. 10-2021-0171392

(51) Int. Cl.
*A61B 5/00* (2006.01)
*A61C 9/00* (2006.01)
*A61C 19/04* (2006.01)

(52) U.S. Cl.
CPC .......... *A61B 5/0059* (2013.01); *A61B 5/0033* (2013.01); *A61B 5/0035* (2013.01);
(Continued)

(58) Field of Classification Search
CPC ... A61B 5/0059; A61B 5/0033; A61B 5/0035; A61B 5/0036; A61B 5/0037;
(Continued)

(56) References Cited

U.S. PATENT DOCUMENTS 10,123,706 B2 * 11/2018 Elbaz .................. H04N 13/246
2008/0062429 A1 * 3/2008 Liang .................... A61B 1/043
356/497
(Continued)

FOREIGN PATENT DOCUMENTS

| EP | 2060227 A1 | 5/2009 |
| EP | 4014846 A1 | 6/2022 |

(Continued)

OTHER PUBLICATIONS

Lee, Jaeyul, et al. "Assessment of the inner surface roughness of 3D printed dental crowns via optical coherence tomography using a roughness quantification algorithm." IEEE Access 8 (2020): 133854-133864. (Year: 2020).*

(Continued)

*Primary Examiner* — Mohamed K Amara
*Assistant Examiner* — Noah J. Haney
(74) *Attorney, Agent, or Firm* — United One Law Group LLC; Kongsik Kim; Jhongwoo Peck

(57) ABSTRACT

An intraoral scanner having a tomography function capable of setting a tomography area using shape information of an oral cavity includes a shape measurement light projector that irradiates shape measurement light for obtaining a shape image of an oral structure; a shape measurement camera that obtains a surface shape image of the oral structure by detecting reflected light; an optical coherence tomography (OCT) body that transmits tomography measurement light to the oral structure and detect reflected light to obtain an internal cross-sectional image of the oral structure; an OCT scan probe that irradiates the tomography measurement light emitted from the OCT body onto a desired position of the oral structure and transfer the reflected light to the OCT body; and a beam splitter that superimposes optical paths of the shape measurement light irradiated from the shape
(Continued)

measurement light projector and the tomography measurement light irradiated from the OCT scan probe.

5 Claims, 9 Drawing Sheets

(52) U.S. Cl.
CPC .......... *A61B 5/0036* (2018.08); *A61B 5/0037* (2013.01); *A61B 5/0066* (2013.01); *A61B 5/0073* (2013.01); *A61B 5/0079* (2013.01); *A61B 5/0088* (2013.01); *A61B 5/4542* (2013.01); *A61B 5/4547* (2013.01); *A61B 5/682* (2013.01); *A61B 5/748* (2013.01); *A61B 5/7485* (2013.01); *A61C 9/0053* (2013.01); *A61C 9/006* (2013.01); *A61C 19/04* (2013.01); *A61B 5/0064* (2013.01); *A61B 5/4848* (2013.01); *A61B 5/6849* (2013.01); *A61B 5/743* (2013.01)

(58) Field of Classification Search
CPC ... A61B 5/0066; A61B 5/0073; A61B 5/0079; A61B 5/0088; A61B 5/4542; A61B 5/4547; A61B 5/682; A61B 5/748; A61B 5/7485; A61B 5/0064; A61B 5/4848; A61B 5/6849; A61B 5/743; A61B 5/066; A61C 9/0053; A61C 9/006; A61C 19/04
USPC .......................................................... 356/497
See application file for complete search history.

(56) References Cited

U.S. PATENT DOCUMENTS

| | | | |
|---|---|---|---|
| 2008/0118886 A1* | 5/2008 | Liang | A61B 5/0088 433/29 |
| 2015/0245770 A1 | 9/2015 | Liang et al. | |
| 2016/0007857 A1* | 1/2016 | Wang | A61B 5/0086 600/425 |
| 2016/0338803 A1* | 11/2016 | Pesach | G06T 7/74 |
| 2017/0280989 A1* | 10/2017 | Heeren | A61B 3/13 |
| 2019/0117075 A1 | 4/2019 | Fan et al. | |
| 2020/0129068 A1 | 4/2020 | Fan et al. | |

FOREIGN PATENT DOCUMENTS

| | | |
|---|---|---|
| KR | 10-1449168 B1 | 10/2014 |
| KR | 10-2088951 B1 | 4/2020 |
| WO | 2017/176300 A1 | 10/2017 |
| WO | 2019/002616 A1 | 1/2019 |
| WO | 2019/005055 A1 | 1/2019 |

OTHER PUBLICATIONS

Hsieh et al., "Dental optical coherence tomography," Sensors (Basel), Jul. 12, 2013, vol. 13, No. 7, pp. 8928-8949, doi: 10.3390/s130708928.

Son, K. et al., "A Comparison Study of Marginal and Internal Fit Assessment Methods for Fixed Dental Prostheses," Journal of Clinical Medicine, Jun. 1, 2019, vol. 8, No. 6, p. 785, https://doi.org/10.3390/jcm8060785.

Chen, R et al., "Quantifying dental biofilm growth using cross-polarization optical coherence tomography," Lett Appl Microbiol, Jun. 1, 2012, vol. 54, No. 6, pp. 537-542, doi: 10.1111/j. 1472-765X.2012.03243.x.

Le, N.M et al., "A noninvasive imaging and measurement using optical coherence tomography angiography for the assessment of gingiva: An in vivo study," J Biophotonics, Dec. 3, 2018, vol. 11, No. 12, doi: 10.1002/ jbio.201800242.

Extended European search report for counterpart EP application No. 22210237.8, dated Aug. 24, 2023.

* cited by examiner (Related Art)

(Related Art)

INTRAORAL SCANNER HAVING TOMOGRAPHIC IMAGING FUNCTION AND METHOD FOR TOMOGRAPHIC IMAGING OF ORAL CAVITY USING THE SAME

CROSS-REFERENCE TO RELATED APPLICATION

This application claims benefit of priority to Korean Patent Application No. 10-2021-0171392 filed on Dec. 3, 2021, the entire contents of which are incorporated herein by reference.

TECHNICAL FIELD

The present invention relates to an intraoral scanner having a tomographic imaging function, and more particularly, to an intraoral scanner having a tomographic imaging function capable of setting a tomography area using shape information of an oral cavity, and an intraoral tomography method using the same.

RELATED ART

Generally, in dental hospitals, teeth or tissue shapes inside an oral cavity of a patient are inspected, and based on such an inspection result, an oral condition of the patient is diagnosed, or a prosthesis is manufactured. In order to obtain teeth and tissue shapes inside an oral cavity, conventionally, an impression taking method using an impression material such as alginate has been used, or a method of obtaining a two-dimensional or three-dimensional shape of an oral structure by irradiating radiation such as X-rays from the outside of an oral cavity has been used. However, it is difficult to obtain an accurate three-dimensional shape of an oral cavity through these methods.

Recently, an optical oral scanner capable of scanning and photographing a shape in an oral cavity of a patient in three dimensions using optical technology and measuring a shape and condition of a mouth of the patient without physical contact has been used. FIG. 1 is a view illustrating an oral shape photographing principle of a typical intraoral scanner. As shown in FIG. 1, the conventional intraoral scanner includes a projector 12 including a light source which irradiates measurement light onto an oral structure S such as a tooth, and a camera 14 including an image sensor which detects light reflected from the oral structure S to obtain a surface shape of the oral structure S. Measurement light (for example, visible light) irradiated from the light source of the projector 12 is irradiated onto the oral structure S in an oral cavity, and light reflected from the oral structure S is detected by the image sensor of the camera 14 to acquire surface shape information of the oral structure S. In this case a two-dimensional image of the oral structure S detected by the camera 14 may be converted into a three-dimensional image using triangulation or the like. That is, the typical intraoral scanner irradiates measurement light onto a desired position inside an oral cavity, detects reflected light generated when the measurement light is reflected from an oral structure, and acquires only surface shape information of the oral structure such as a tooth.

When the typical intraoral scanner is used, since an internal state of the oral structure S cannot be inspected, a method of obtaining an internal tomography image of the oral structure S using an optical coherence tomography (OCT) device is known (see Korean Patent Application No. 10-2020-0175365). FIG. 2 is a view illustrating a method of obtaining an internal tomography image of an oral structure S using a typical OCT scanner. As shown in FIG. 2, a typical OCT scanner includes an OCT body which transmits measurement light (for example, near-infrared light) to an oral structure S such as a tooth, detects reflected light (scattered light) reflected inside the oral structure S and each monolayer, and obtains an internal cross-sectional image of the oral structure S, and an OCT scan probe 24 which irradiates the measurement light emitted from the OCT body 22 onto a desired position of the oral structure S and transmits reflected light reflected from the oral structure S to the OCT body 22. The OCT body 22 is a typical device that acquires tomography information inside an object using a coherence property of measurement light. The OCT scan probe 24 may include a collimator 24a which concentrates measurement light and reflected light, a reflection mirror 24b which reflects the concentrated measurement light to a desired photographing position of the oral structure S and transmits reflected light reflected from the oral structure S to the collimator 24a, and an objective lens 24c which concentrates the measurement light reflected from the reflection mirror 24b at the desired photographing position of the oral structure S. Here, as the reflection mirror 24b, a micro electro mechanical system (MEMS) mirror capable of sequentially scanning photographing positions of the oral structure S by adjusting a reflection angle of measurement light may be used.

Since the OCT scanner obtains a tomography image of an object to be measured based on one line scan in a depth direction (z direction) and one lateral direction (x or y direction) of the object to be measured, it is not easy to obtain a tomography image of the entirety of the object to be measured. In addition, since the OCT scan probe 24 is a hand-held probe, when an image of an intraoral structure is obtained using the OCT scan probe 24, an OCT area is small, and a tomography image of a desired position is difficult to accurately obtain.

RELATED ART DOCUMENTS

1. Korean Patent Registration No. 10-2088951
2. Korean Patent Registration No. 10-1449168
3. International Patent Publication WO 2019/005055
4. International Patent Publication WO 2019/002616
5. International Patent Publication WO 2017/176300
6. European Patent Publication EP 2060227 A1
7. Sensors (Basel) 2013 July; 13(7): 8928-8949, Dental Optical Coherence Tomography (https://www.ncbi.nlm.nih.gov/pmc/articles/PMC3758630)
8. J. Clin. Med. 2019, 8(6), 785. A Comparison Study of Marginal and Internal Fit Assessment Methods for Fixed Dental Prostheses (https://www.mdpi.com/2077-0383/8/6/785)
9. Letters in Applied Microbiology, Volume 54, Issue 6, June 2012, 537-542, Quantifying dental biofilm growth using cross-polarization optical coherence tomography (https://sfamjournals.onlinelibrary.wiley.com/doi/full/10.1111/j.1472-765X.2012.03243.x)
10. Journal of Biophotonics, Volume 11, Issue 12, December 2018, e201800242, A noninvasive imaging and measurement using optical coherence tomography angiography for the assessment of gingiva: An in vivo study (https://onlinelibrary.wiley.com/doi/full/10.1002/jbio.201800242)

SUMMARY

Technical Objects

It is an object of the present invention to provide an intraoral scanner having a tomography function capable of obtaining a tomography image inside an oral cavity by combining an optical coherence tomography (OCT) device, and an intraoral tomography method using the same.

It is another object of the present invention to provide an intraoral scanner having a tomography function capable of effectively obtaining a tomography image of a desired position, and an intraoral tomography method using the same.

Technical Solutions

In order to achieve the objects above, the present invention provides an intraoral scanner, which has a tomography function, including a shape measurement light projector (12) configured to irradiate shape measurement light for obtaining a shape image of an oral structure; a shape measurement camera (14) configured to obtain a surface shape image of the oral structure by detecting reflected light formed when the shape measurement light is reflected from a surface of the oral structure; an optical coherence tomography (OCT) body (22) configured to transmit tomography measurement light to the oral structure and detect reflected light reflected inside the oral structure S to obtain an internal cross-sectional image of the oral structure; an OCT scan probe (24) configured to irradiate the tomography measurement light emitted from the OCT body (22) onto a desired position of the oral structure and transfer the reflected light reflected from the oral structure to the OCT body (22); and a beam splitter (30) configured to superimpose optical paths of the shape measurement light irradiated from the shape measurement light projector (12) and the tomography measurement light irradiated from the OCT scan probe (24).

The present invention also provides an intraoral tomography method including sequentially irradiating pieces of shape measurement light onto an oral structure, detecting reflected light formed when the shape measurement light is reflected from a surface of the oral structure, and obtaining an entire image (T) of the oral structure; setting a position of a region of interest (ROI) requiring tomography for the entire image (T) of the oral structure; and transmitting tomography measurement light along the set ROI, detecting reflected light reflected inside the ROI, and obtaining an internal cross-sectional image of the ROI.

DETAILED DESCRIPTION

Figure 1:
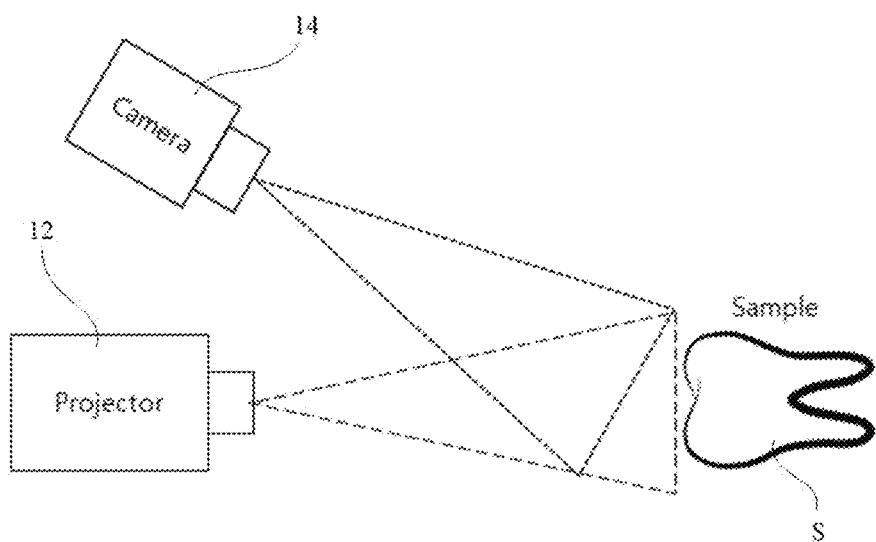
FIG. 1 is a view illustrating an oral shape photographing principle of a typical intraoral scanner.
Figure 2:
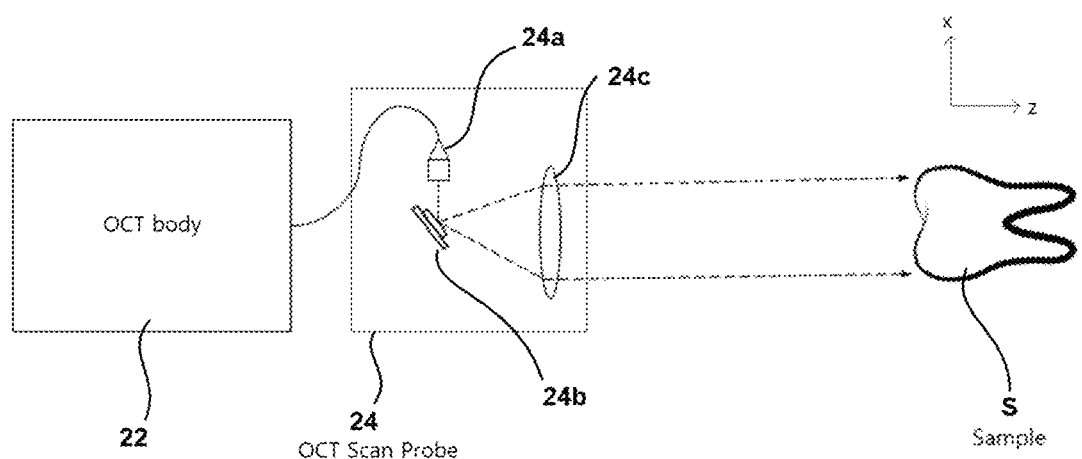
FIG. 2 is a view illustrating a method of obtaining an internal tomography image of an oral structure using a typical optical coherence tomography (OCT) scanner.

Hereinafter, the present invention will be described in detail with reference to the accompanying drawings. In the accompanying drawings, elements performing the same or similar functions as in a related art are assigned the same reference numerals.

Figure 3:
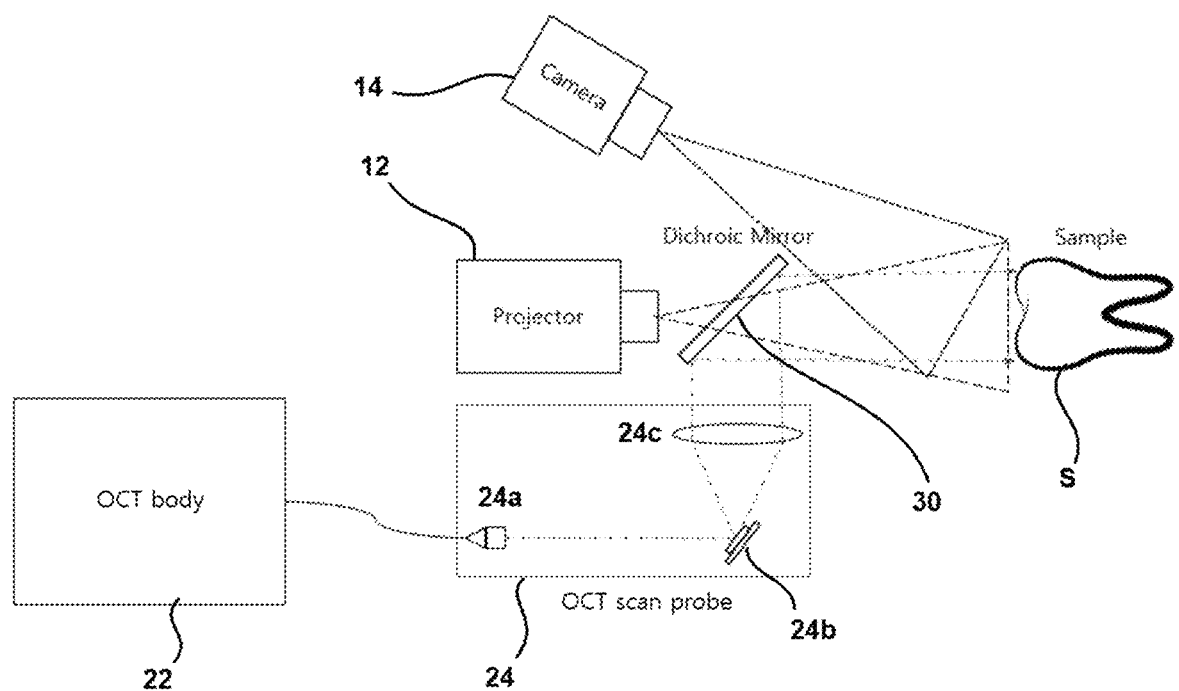
FIG. 3 is a view illustrating a configuration of an intraoral scanner having a tomography function according to one embodiment of the present invention.

FIG. 3 is a view illustrating a configuration of an intraoral scanner having a tomography function according to one embodiment of the present invention. As shown in FIG. 3, the intraoral scanner having the tomography function according to the present invention includes a shape measurement light projector 12, a shape measurement camera 14, an optical coherence tomography (OCT) body 22, an OCT scan probe 24, and a beam splitter 30. The shape measurement light projector 12 irradiates shape measurement light for obtaining a shape image of an oral structure S such as a tooth. As the shape measurement light, measurement light capable of obtaining the shape image of the oral structure S may be used without limitation, and preferably, visible light, for example, visible light having a wavelength of 400 nm to 700 nm, may be used. The shape measurement camera 14 is a device for obtaining a surface shape image of the oral structure S by detecting reflected light formed when the shape measurement light is reflected from a surface of the oral structure S and includes a typical image sensor. In operation, the shape measurement light is output from the shape measurement light projector 12, the output shape measurement light passes through the beam splitter 30 to then be irradiated onto the oral structure S, and reflected light reflected from the oral structure S is detected by the shape measurement camera 14, thereby obtaining the surface shape image of the oral structure S. In this case, a two-dimensional (2D) image of the oral structure S obtained by the shape measurement camera 14 may be converted into a three-dimensional (3D) image using triangulation or the like.

The OCT body 22 transmits tomography measurement light (for example, near infrared light) to the oral structure S and detects reflected light (scattered light) reflected inside the oral structure S, specifically, from each monolayer, to obtain an internal cross-sectional image of the oral structure S. The OCT body 22 is a typical device which acquires tomography information inside an object using a coherence property of tomography measurement light. For example, the tomography measurement light may be broadband low-coherence light having a short coherence length and preferably may be near-infrared light, specifically, near-infrared light having a wavelength of 750 nm to 1,500 nm. The OCT scan probe 24 is a device which irradiates the tomography measurement light emitted from the OCT body 22 onto a desired position of the oral structure S and transmits reflected light reflected from the oral structure S to the OCT body 22. The OCT scan probe 24 may include a collimator 24a which concentrates the tomography measurement light and reflected light thereof, a reflection mirror 24b which reflects concentrated measurement light to a desired photographing position of the oral structure S and transmits reflected light reflected from the oral structure S to the collimator 24a, and an objective lens 24c which concentrates measurement light reflected from the reflection mirror 24b at the desired photographing position of the oral structure S. Here, as the reflection mirror 24b, a micro electro mechanical system (MEMS) mirror capable of sequentially scanning photographing positions of the oral structure S by adjusting a reflection angle of the tomography measurement light may be used. For example, the reflection mirror 24b is rotated based on two axes (for example, an x axis and a y axis having an orthogonal relationship) to sequentially scan planes on which the oral structure S is positioned, the tomography measurement light is irradiated into the oral structure S in a direction perpendicular to the plane (z axis direction orthogonal to the x axis and y axis), thereby obtaining a 3D tomography image of the oral structure S.

The beam splitter 30 is a device for superimposing optical paths of the shape measurement light emitted from the shape measurement light projector 12 and the tomography measurement light emitted from the OCT scan probe 24 and superimposes a shape acquisition optical system formed by the shape measurement light projector 12 and the shape measurement camera 14 and a tomography acquisition optical system formed by the OCT body 22 and the OCT scan probe 24. For example, as shown in FIG. 3, the beam splitter 30 may be a dichroic mirror 30 which transmits the shape measurement light emitted from the shape measurement light projector 12 and reflects the tomography measurement light emitted from the OCT scan probe 24 to irradiate the shape measurement light and the tomography measurement light onto the oral structure S and separate and transmit pieces of reflected light to the shape acquisition optical system (specifically, the shape measurement camera 14) and the tomography acquisition optical system (specifically, the OCT body 22). Since the shape acquisition optical system formed by the typical shape measurement light projector 12 and shape measurement camera 14 and the tomography acquisition optical system formed by the typical OCT body 22 and OCT scan probe 24 use pieces of measurement light in different areas, the same optical path cannot be used. However, as shown in FIG. 3, when the dichroic mirror 30 which reflects the tomography measurement light and transmits the shape measurement light is positioned at a position through which the shape measurement light of the shape measurement light projector 12 passes and which is not included in a field of view (FoV) area of the shape measurement camera 14, it is possible to form an integrated optical system in which measurement areas of the shape acquisition optical system and the tomography optical system, that is, regions of interest (ROIs), are superimposed. Therefore, the dichroic mirror 30 may superimpose and irradiate the shape measurement light and the tomography measurement light onto the oral structure S so that both an external surface shape image and an internal tomography image of the oral structure S can be obtained.

In the intraoral scanner having the tomography function according to one embodiment of the present invention, a position of an ROI requiring tomography can be set for an entire image T of the oral structure obtained by the shape measurement camera 14. A position of a partial image p of the oral structure in which the ROI is set is detected, tomography measurement light is transmitted to the position of the partial image p, and light reflected from the position of the partial image p is detected, thereby obtaining an internal cross-sectional image of the ROI.

Figure 4:
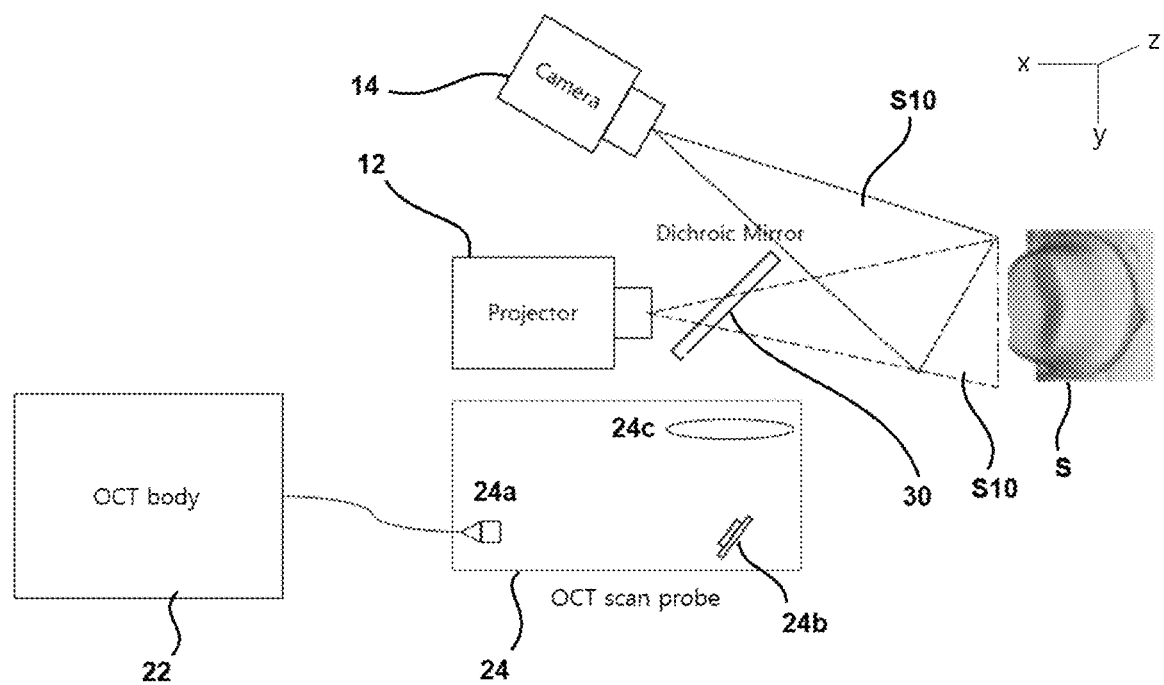
FIGS. 4 to 7 are views for describing an intraoral tomography method using an intraoral scanner having a tomography function according to the present invention.
Figure 5:
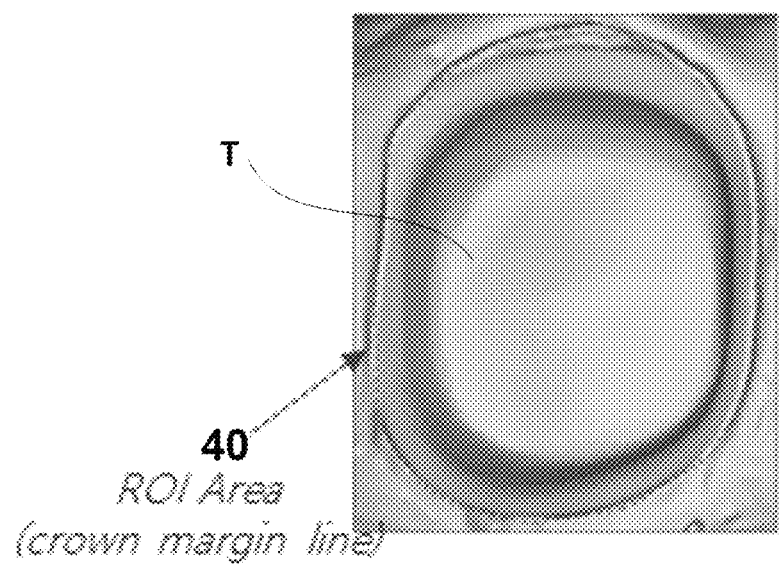
Figure 6:
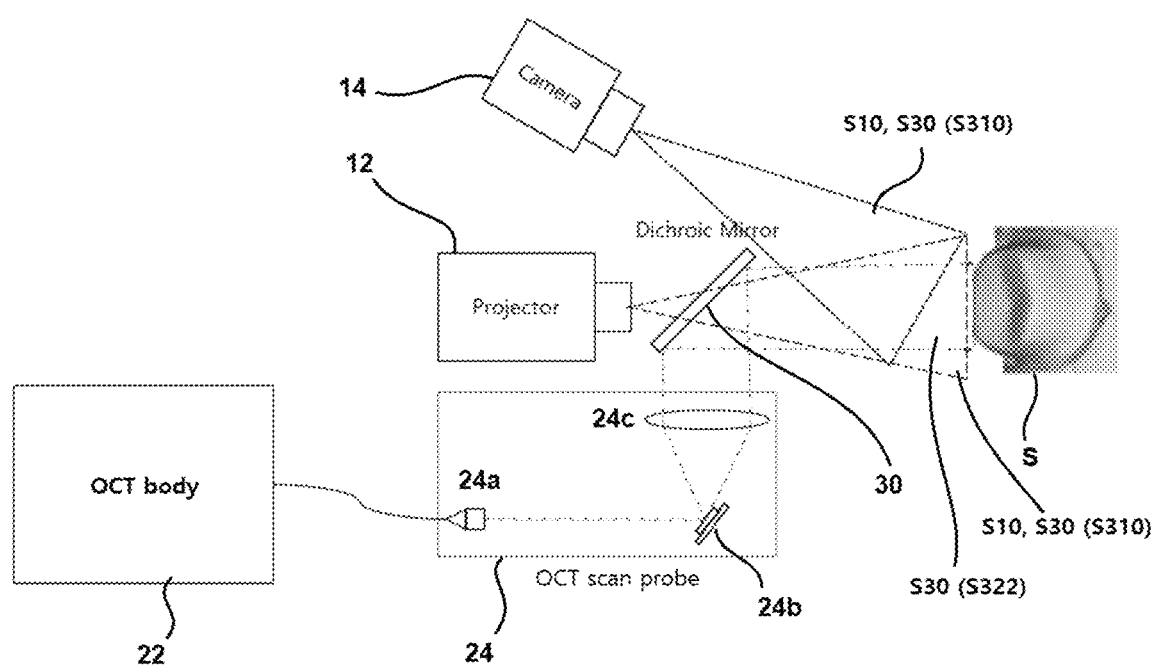
Figure 7:
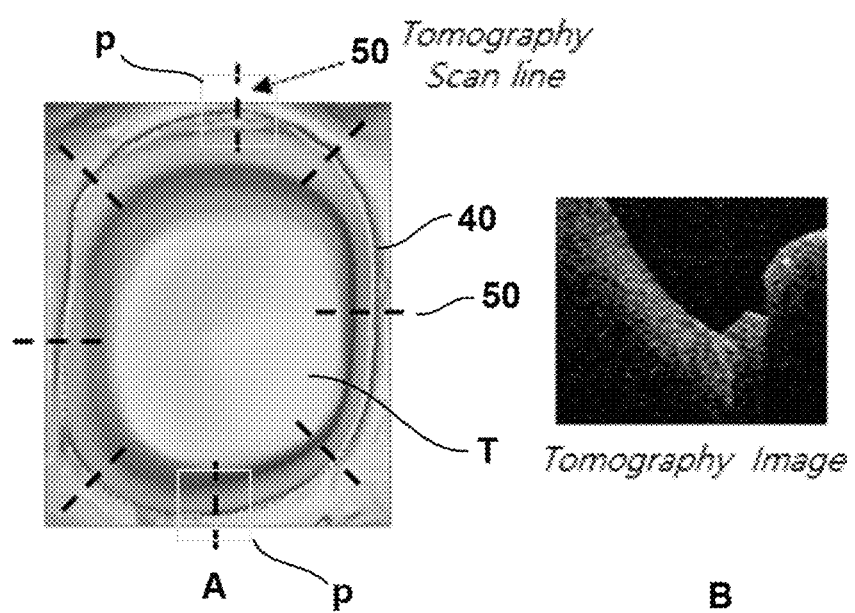
Figure 8:
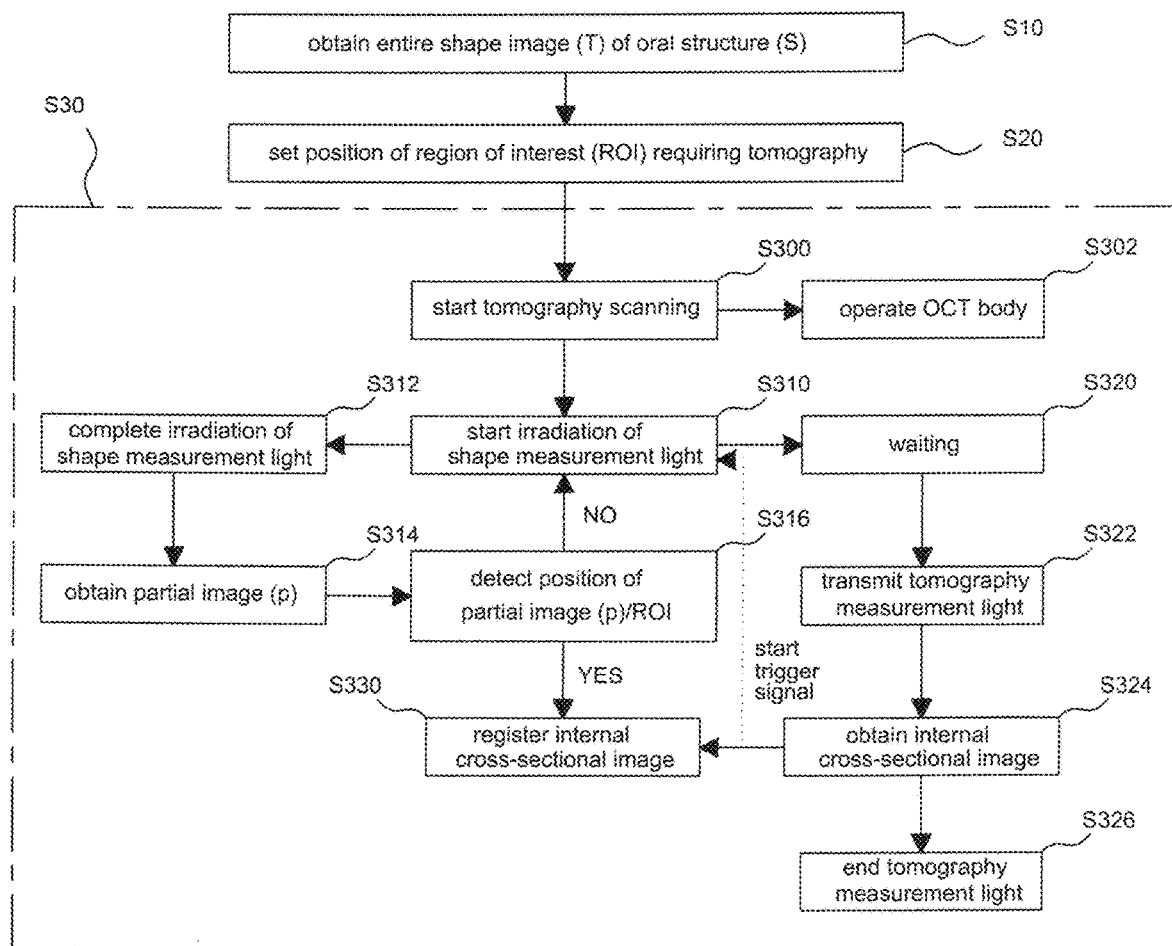
FIG. 8 is a flowchart for describing the intraoral tomography method according to one embodiment of the present invention.

FIGS. 4 to 8 are views for describing an intraoral tomography method using an intraoral scanner having a tomography function according to the present invention. According to the present invention, in order to obtain a tomography image, first, as shown in FIGS. 4 and 8, pieces of shape measurement light are sequentially irradiated onto an oral structure S using a shape measurement light projector 12, and reflected light formed when the shape measurement light is reflected from a surface of the oral structure S is detected using a shape measurement camera 14 to obtain an entire image T of the oral structure S (S10). Here, the entire image T of the oral structure S is an entire surface image T of the oral structure S including an ROI, for example, a surface shape image T of one entire tooth. FIG. 5 is a view illustrating an example of data about a 3D surface shape image T of the oral structure S obtained by performing surface scanning in this way. A position of an ROI requiring tomography is set for the obtained entire surface shape image T of the oral structure S (S20, ROI set-up). For example, as shown in FIG. 5, a position of a crown margin line 40 is marked as the ROI on the 3D surface shape image T of the oral structure S such as a tooth.

Next, as shown in FIG. 6, tomography measurement light is transmitted along the set ROI using an OCT body 22 and an OCT scan probe 24, reflected light, which is reflected inside the ROI, specifically, from each monolayer therein, is detected, that is, tomography scanning is performed on the ROI to obtain an internal cross-sectional image of the ROI (S30). FIG. 7 is a view illustrating an example in which tomography scanning is performed on an ROI. As shown of FIG. 7A, tomography scanning is not performed on an entire oral structure S and is performed on a portion of the oral structure S according to the ROI, that is, only a tomography area 50 (portion indicated by a dotted line). FIG. 7B is an image showing an example of a tomography image of the oral structure S obtained at a positioned in the ROI. Therefore, according to the present invention, the ROI set in the entire surface shape image T of the oral structure S serves to guide a path or area in which tomography scanning is performed. In this case, a position of a partial image p of the oral structure in which the ROI is set is detected, tomography measurement light is transmitted to the position of the partial image p, and reflected light reflected at the position of the partial image p is detected, thereby obtaining an internal cross-sectional image of the ROI.

According to a more specific embodiment of the present invention, operation S30 of obtaining the internal cross-sectional image of the ROI includes the following operations. As shown in FIGS. 6 to 8, tomography scanning (OCT scan) starts according to a user's command or a preset program (S300, OCT mode). In this case, when power is not applied to the OCT body 22 or the OCT body 22 is not ready for use, the OCT body 22 is operated to convert the OCT body 22 to a measurable state (S302).

When the tomography scanning (OCT scan) starts, first, by using the shape measurement light projector 12, shape measurement light is irradiated onto a certain position of the oral structure S, that is, a part of the oral structure S, and reflected light formed when the shape measurement light is reflected from a surface of the part of the oral structure S is detected using the shape measurement camera 14 (S310). When the irradiation of the shape measurement light onto the part of the oral structure S is completed (S312), the partial image p (see FIG. 7) of the oral structure S is obtained (S314). The obtained partial image p of the oral structure S is a 3D surface image of the part of the oral structure S, and in this specification, the partial image p is referred to as "patch data" as necessary. Next, the partial image p of the oral structure S obtained in operation S314 is compared with the entire image T of the oral structure S obtained in operation S10 to detect a position of the partial image p in the entire image T of the oral structure S and detect whether the ROI is present in the partial image p (S316). As described above, the partial image p of the oral structure S being compared with the entire image T of the oral structure S to detect the position of the partial image p in the entire image T of the oral structure S is referred to as "global registration" for convenience.

Meanwhile, when the irradiation of the shape measurement light is completed (S312), the OCT body 22 transmits tomography measurement light to the part of the oral structure S onto which the shape measurement light has been irradiated (S322), and reflected light (scattered light) reflected inside the oral structure S is detected to obtain an internal cross-sectional image of the oral structure S is obtained (S324). For example, at the same time when the shape measurement light is irradiated onto the part of the oral structure S (S310), a measurement signal (trigger signal) is transmitted to the OCT body 22, and until the irradiation of the shape measurement light is completed (S312), the OCT body 22 performs a waiting mode in which tomography measurement light is not irradiated (S320). When the waiting mode (S320) ends, the tomography measurement light may be transmitted to the part of the oral structure S onto which the shape measurement light has been irradiated (S322), and reflected light (scattered light) reflected inside the oral structure S may be detected to obtain an internal cross-sectional image of the oral structure S (S324). Here, an obtained 2D cross-sectional image obtained (2D tomography image, for example, see FIG. 7B) is referred to as an "OCT B-scan image." As described above, after the internal cross-sectional image of the oral structure S is obtained, the irradiation of the tomography measurement light is ended (S326). As shown in FIG. 7, it is preferable that the number of internal cross-sectional images obtained is one for one partial image p of the oral structure S, and if necessary, a plurality of, for example, two to five cross-sectional images, may be obtained at equal intervals.

In the present invention, shape measurement light and tomography measurement light are not irradiated simultaneously but are irradiated alternately with each other, and preferably, the tomography measurement light is irradiated immediately after the irradiation of the shape measurement light is completed. When tomography measurement light of the OCT body 22 is irradiated simultaneously when shape measurement light is irradiated to obtain the partial image p (see FIG. 7) of the oral structure S, since reflected light of the shape measurement light cannot be detected correctly due to the interference of the tomography measurement light, it is difficult to obtain the correct partial image p. In one embodiment of the present invention, a shape measurement time required until the irradiation of the shape measurement light is completed (S312) to obtain one partial image p after the shape measurement light is irradiated (S310) varies according to the performance of the shape measurement light projector 12 and the shape measurement camera 14 and is usually a constant short time of several tens of milliseconds (ms). Therefore, after a trigger signal is transmitted to the OCT body 22, a time during which the OCT body 22 is in a waiting mode may be set to be equal to the "shape measurement time." When an irradiation time of the shape measurement light and an irradiation time of the tomography measurement light are superimposed on each other, as described above, it is difficult to obtain the correct partial image p due to light interference. On the other hand, when a time difference between the irradiation of shape measurement light and the irradiation of tomography measurement light is large, due to the characteristics of a hand-held device, a position of the device is changed, and thus a position at which the partial image p is obtained is different from a position at which a tomography image is obtained, which makes it difficult to obtain the tomography image at a correct position.

Next, in operation S316 of detecting the position of the partial image p, when the ROI is present in the partial image p, the cross-sectional image of the part of the oral structure S obtained in operation S324 is used as an internal cross-sectional image of the position of the partial image p, specifically, the ROI of the partial image p (S330, OCT image registration). That is, in the entire image T, an internal cross-sectional image of a position at which the current partial image p is obtained is registered, that is, stored, in a memory (not shown) inside the scanner. On the other hand, when the ROI is not present in the partial image p, the cross-sectional image of the oral structure S obtained in step S324 is discarded. In the present invention, since the partial image p of the oral structure S is temporary data and patch data for checking whether a cross-sectional image obtained at a corresponding partial position is a cross-sectional image of an ROI and for identifying a position at which the corresponding cross-sectional image is obtained, after the cross-sectional image of the corresponding position (that is, the position of the partial image p) is registered or discarded, the partial image p of the oral structure S may be discarded without being separately stored.

As described above, after a cross-sectional image of one part is obtained, and then registered or discarded, the intraoral scanner may be moved to a next position, that is, another part of the oral structure S, a start trigger signal may be transmitted to the shape measurement light projector 12 to repeat the above described processes. Thereby, an entire ROI set in the entire image T of the oral structure may be detected to detect an internal cross-sectional image of the ROI.

According to the present specific embodiment, based on information about the obtained surface shape image T of the oral structure S, when an ROI is present in the image p of a specific part of the oral structure S, a tomography image obtained from the specific part of the oral structure S is used. When the ROI is not present in the image p of the specific part of the oral structure S, a tomography image obtained from the specific part of the oral structure S is discarded, thereby quickly and effectively obtaining a necessary tomography image of a part. According to an embodiment of the present invention, the surface shape image T of the oral structure S is obtained using shape measurement light, and the ROI is extracted or specified in the obtained surface shape image T. Next, the partial image p is obtained by partially scanning the oral structure S again using shape measurement light, and when a position of the obtained partial image p is a position including an ROI, a tomography image is obtained at the corresponding positioned. When the position of the obtained partial image p does not include the ROI, the tomography image obtained at the corresponding positioned is discarded.

Figure 9:
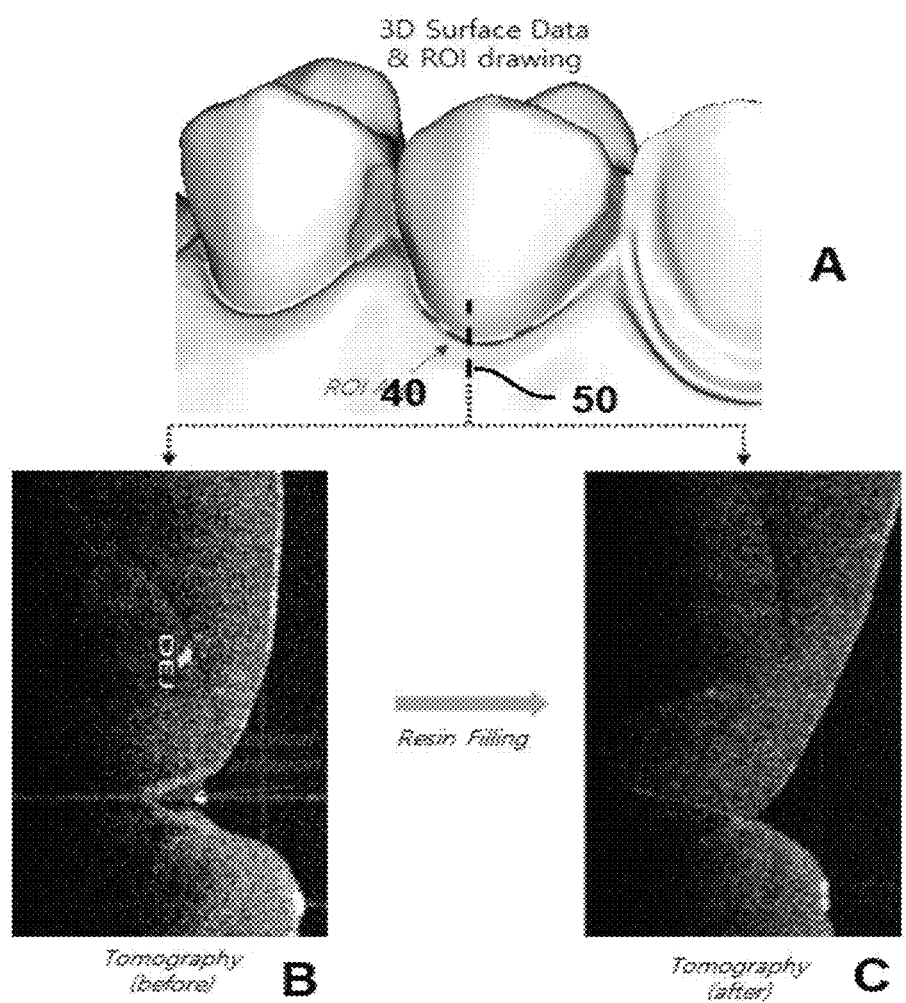
FIG. 9 is a view illustrating an example of performing tomography on a specific region of interest in an oral cavity according to the present invention.

FIG. 9 is a view illustrating an example of performing tomography on a specific ROI in an oral cavity according to the present invention. In the example shown in FIG. 9, a wear position at which tooth wear occurs is set as an ROI 40, and tomography is performed on a tomography area 50 formed along the ROI 40 (see FIG. 9A). Tomography results obtained at a specific position of the ROI 40 are shown in FIGS. 9B and 9C. FIG. 9B shows a cross-sectional shape of a worn tooth before treatment as the tomography result, and FIG. 9C shows a cross-sectional shape of a worn portion of a tooth filled with a resin after treatment as the tomography result.

According to an intraoral scanner having a tomography function and an intraoral tomography method using the same, by combining an OCT device, a tomography image inside an oral cavity can be obtained, and in particular, only a tomography image of a desired position inside the oral cavity can be effectively obtained.

Although the present invention has been described above with reference to the accompanying drawings and exemplary embodiments, the present invention is not limited to what is shown in the drawings and the embodiments described above. Reference numerals are labeled in the following claims to aid understanding, but the scope of the following claims is not limited to the reference numerals and what is shown in the drawings, and should be construed to encompass all modifications, equivalent constructions and functions of the exemplary embodiments.

The invention claimed is:

1. An intraoral tomography method comprising:
   sequentially irradiating pieces of shape measurement light onto an oral structure, detecting reflected light formed when the shape measurement light is reflected from a surface of the oral structure, and obtaining an entire image (T) of the oral structure;
   setting a position of a region of interest (ROI) requiring tomography for the entire image (T) of the oral structure;
   transmitting tomography measurement light along the set ROI, detecting reflected light reflected inside the ROI, and
   obtaining an internal cross-sectional image of the ROI, wherein the internal cross-sectional image of the ROI is obtained by steps comprising:
   irradiating the shape measurement light onto a part of the oral structure(S), detecting reflected light formed when the shape measurement light is reflected from a surface of the part of the oral structure(S), and obtaining a partial image (p) of the oral structure;
   comparing the partial image (p) of the oral structure(S) with the entire image (T) of the oral structure(S), detecting a position of the partial image (p) in the entire image (T) of the oral structure(S), and detecting whether the ROI is present in the partial image (p);
   transmitting the tomography measurement light to the part of the oral structure(S) onto which the shape measurement light has been irradiated, detecting reflected light reflected inside the oral structure(S), and obtaining an internal cross-sectional image of the oral structure(S); and
   when the ROI is present in the partial image (p), registering the internal cross-sectional image, which is obtained from the part of the oral structure(S) onto which the shape measurement light has been irradiated, as the internal cross-sectional image of the ROI of the partial image (p).

2. The intraoral tomography method of claim 1, wherein the ROI set in a surface shape image of the oral structure guides a path or area in which tomography is performed.

3. The intraoral tomography method of claim 1, wherein the shape measurement light and the tomography measurement light are not irradiated simultaneously, and the tomography measurement light is irradiated immediately after irradiation of the shape measurement light is completed.

4. The intraoral tomography method of claim 1, wherein, when the ROI is not present in the partial image (p), the internal cross-sectional image, which is obtained from the part of the oral structure(S) onto which the shape measurement light has been irradiated, is discarded.

5. The intraoral tomography method of claim 1, wherein, after a cross-sectional image of the position of the partial image (p) is registered, the partial image (p) of the oral structure(S) is discarded without being separately stored.

* * * * *